United States Patent

Baldwin et al.

[11] 3,941,019
[45] Mar. 2, 1976

[54] METHOD AND APPARATUS FOR CUTTING LUMBER AND THE LIKE

[75] Inventors: Ralph B. Baldwin, East Grand Rapids; James T. Visser, Grand Rapids, both of Mich.

[73] Assignee: Oliver Machinery Company, Grand Rapids, Mich.

[22] Filed: May 9, 1973

[21] Appl. No.: 358,814

[52] U.S. Cl. ................. 83/71; 83/268; 83/468; 144/312
[51] Int. Cl.² .......................................... B26D 5/02
[58] Field of Search ......... 83/268, 71, 468; 144/312

[56] References Cited
UNITED STATES PATENTS

| 3,186,453 | 6/1965 | Green ................................. 83/250 |
| 3,329,181 | 7/1967 | Buss et al............................... 83/34 |
| 3,459,246 | 8/1969 | Ottosson ......................... 144/312 R |
| 3,736,968 | 6/1973 | Mason............................. 144/312 R |
| 3,811,353 | 5/1974 | Miles ................................... 83/71 |

*Primary Examiner*—Donald R. Schran
*Attorney, Agent, or Firm*—Price, Heneveld, Huizenga & Cooper

[57] ABSTRACT

An in-feed conveyor brings individual pieces of lumber to an examining area, where a carriage is movably mounted relative to the conveyor for movement along the piece of stock. A control on the carriage is triggered whenever the carriage is positioned in predetermined alignment with defects in the stock, including undesirable end portions as well as structural or quality defects intermediate the ends of the piece. Triggering such control sends an input to a computer, which controls the cutting of the stock by a saw located downstream from the examining station, by which the defects are cut out of the piece of stock. The computer completely controls the incremental movement of the piece of stock at the saw, automatically stopping the stock and causing the same to be cut, not only to remove defects, but also to produce an optimum yield of different pieces cut from the good stock between the defects. Such optimum yield is computed by the computer based on the stock defect information fed to the computer during examination of each piece of stock, as well as on the contents of a manifest or list of desired pieces entered into the computer as a preliminary step, and as a function of predetermined priorities, as for example the longest obtainable pieces. The computer has a variable waste allowability parameter, so that selection of different amounts of tolerable or allowable waste in cutting the stock can correspondingly vary the nature of the optimum yield computed by the computer. A clamping and feeding apparatus very securely holds the stock in position with respect to the saw, both during the actual cutting and also during the advancement of the stock with respect to the saw, so that the stock cannot inadvertantly move during either such operation.

22 Claims, 10 Drawing Figures

METHOD AND APPARATUS FOR CUTTING LUMBER AND THE LIKE

BACKGROUND OF THE INVENTION

This invention relates to mechanized, or automated, stock-handling and cutting apparatus, particularly for cutting lumber to remove defects and to produce pieces of particular dimensions in accordance with a manifest. More particularly, the invention relates to a complete examination, transporting and cutting system in which a computer is fed data from an examination station relative to the location of defects along the length of a piece of lumber, and the computer then controls the complete sequence of advancing the lumber to a crosscut saw, stopping the stock for cutting at different places to ultimately produce the optimum yield and to remove the defects from each particular piece of stock, controlling the operation of the saw as well as that of a conveyor means which advances the stock relative to the saw.

The concept of automatic, machine-operated "defecting", or defect-removal, together with really precise and accurate optimum yield computation and cutting is one which has long been needed and in a general way long sought after in the lumbering and lumber-handling industries, as an indistinct ultimate goal. In partial satisfaction of such a goal, a number of devices have been proposed heretofore which were at least useful advances. For example, there have been systems proposed in which the stock was transported more or less automatically, by use of conveyors and the like, to an examining station and to a cutting station, where different individuals specialized in different tasks and were thus more efficient, one examining and marking the lumber where cutting was to take place, and the other sawing at the indicated marks. Subsequently, more inventive systems were advanced as for example systems in which the lumber is marked with machine-readable indicia at an examining station, and then transported through an automated sawing station which responds to such indicia automatically, sawing wherever each such indicia appears. A good example of a very effective type of such apparatus is disclosed in U.S. Pat. No. 3,780,777 assigned to Oliver Machinery Co. assignee herein.

Another type of system which has been proposed is illustrated in U.S. Pat. No. 3,329,181, in which the lumber itself is not actually marked, but instead, the "marking" or examining apparatus sends signals to a computer concerning the defects in a piece of stock, and the computer then indicates to a human sawer where cuts should be made. In this apparatus, however, all stock handling is done manually during the cutting operation, as is the actual operation of the saw.

SUMMARY OF THE INVENTION

From the foregoing background, it will readily be seen that there has indeed been a long-felt need in the art for a more complete and more automatic, as well as more accurate, apparatus for defecting lumber and for dividing the latter into optimum sizes on a more accurate and consistent, and more dependable basis, i.e., a system in which the lumber or stock is not subject to significant amounts of human handling, in which the lumber is machine-controlled the majority of the time and, very importantly, in which a relatively large number of different lengths of desired pieces can accurately be produced on an optimum yield basis, accurately and dependably, according to actual computations for each different piece of stock supplied, having its own particular set of defects. The present invention provides, as a major object, automated such apparatus which satisfies the requirements just stated, and provides the concomitant advantages.

Among the more particular objects and advantages of the invention are: to provide apparatus of the type just noted, and in which control of the stock after examination for defects and the like is completely automated and, furthermore, is very accurately controlled, for accurate cutting. Furthermore, in accordance with the invention, even the cutting is automatically performed.

A further object of great importance to the invention, is the use of a computer to determine the points where cutting should occur to produce an optimum yield of pieces in accordance with a desired manifest or listing, and furthermore, the computing of optimum yield by use of a variable selective "bias" or tolerance for otherwise good stock which is wasted in cutting the stock to produce the optimum yield.

Numerous other objects and advantages of the invention will become apparent upon consideration of the following specification and the drawings, a brief description of which is as follows:

DESCRIPTION OF THE PREFERRED EMBODIMENT

Figure 1:
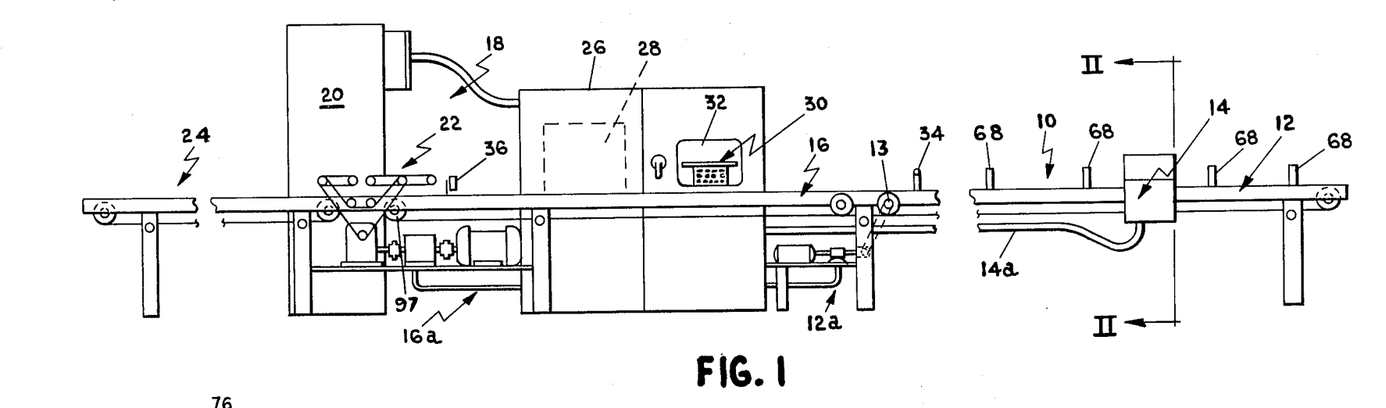
FIG. 1 is a simplified fragmentary, overall front elevation of apparatus embodying the invention, shown on a reduced scale.

Referring now in more detail to the drawings, FIG. 1 illustrates in a somewhat generalized pictorial manner, the overall nature of the apparatus and its different major parts. These include, basically, an examining station 10 which includes an intermittently-operated conveyor device 12 and a movable carriage 14 mounted upon the conveyor (in a manner explained more fully hereinafter), and movable lengthwise along the same; also, the apparatus includes a stock-advancing in-feed conveyor 16 in longitudinal alignment with conveyor 12 but driven separately therefrom, as well as a cutting station 18 having a cabinetenclosed saw 20 as well as an array of roller means 22, to be described in more detail hereinafter, for forceably engaging, clamping and advancing stock incrementally past the cutting station. Further, the apparatus includes an outfeed conveyor 24 and, very importantly, an equipment cabinet or console 26 housing a digital computer illustrated pictorially at 28, which controls practically all phases of operation of the apparatus, as will be explained, and to which is connected the different parts of the apparatus, including for example, the conveyor 12 (by its independent drive 12a), the movable carriage 14 (as by a flexible cable harness 14a), the independent drive 16a for conveyor 16 and, conjointly, roller means 22, the saw 20, etc. Computer 28 may advantageously be of the type manufactured and sold by Digital Equipment Co. and identified as model or series "pdp 8" or by General Automation, Inc. and identified as model "SPC-16", such commercially-available computers being entirely capable of the different routines necessary for complete and satisfactory operation of the system as disclosed herein. The computer 28 has a data input terminal, preferably a teletype unit 30, which is preferably made visible from outside cabinet 26 through a window 32 therein. As will be recognized, such an input terminal is advantageous not only for providing a familiar typewriter-type keyboard input for entering data and commands into the computer, but also for providing a physical printout which may be utilized, for example, to list at any time the progress which the apparatus has then made toward fulfilling a desired manifest of pieces to be cut. As a final matter, the apparatus of FIG. 1 embodies a barrier means or gate 30 and a physically similar but operationally different gate or stock-sensor 38.

Figure 2:
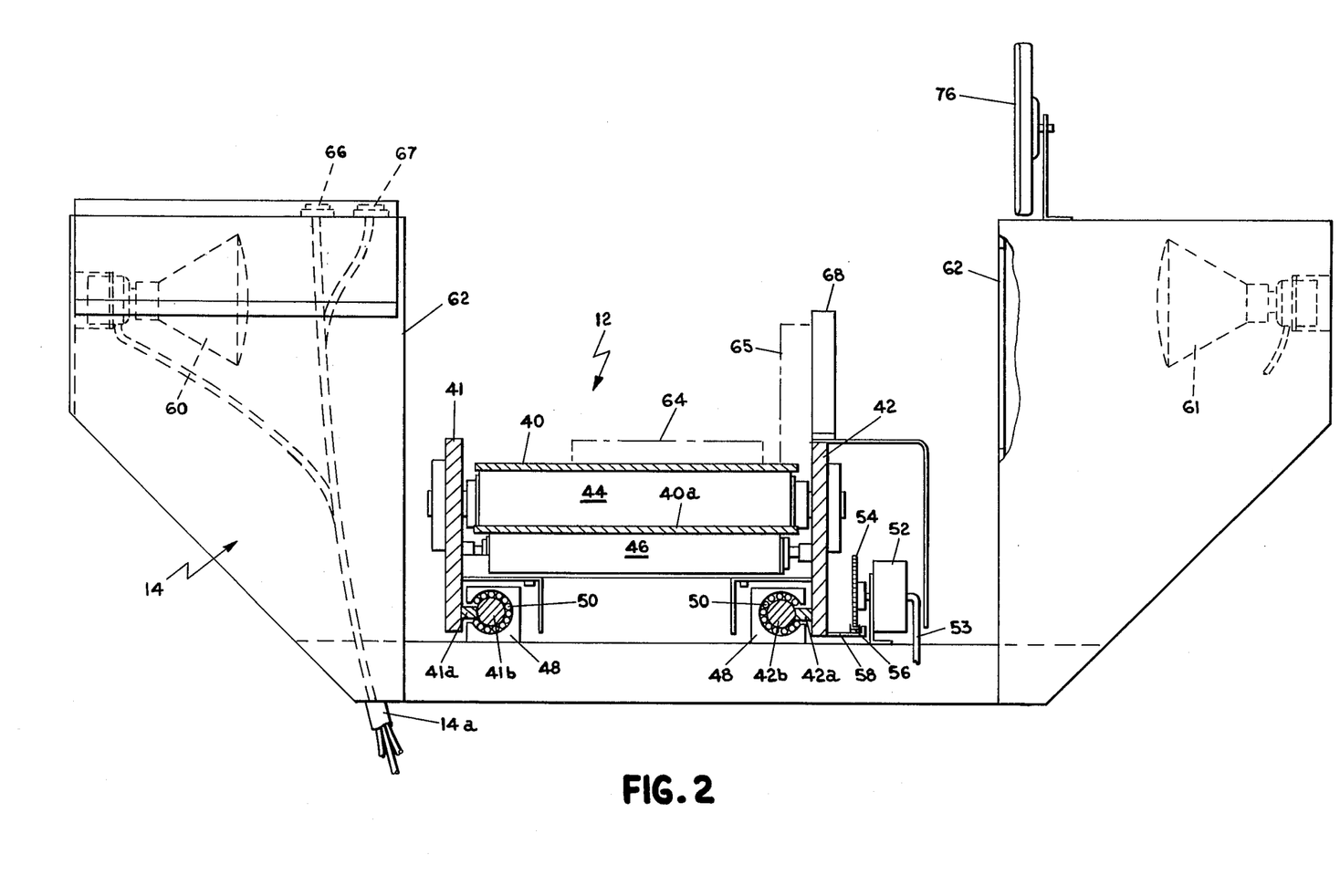
FIG. 2 is an enlarged sectional end elevation, taken through the plane II—II of FIG. 1.

The conveyor 12 located at the examining station 10 may be practically any desired type of lumber transport, but is very effectively implemented by means of a belt-type conveyor as illustrated in more detail in FIG. 2, wherein the endless belt member for such conveyor is designated by the numeral 40, the same preferably being of a known type having a thread or fabric core which is impregnated with and covered by a rubbery coating, preferably one with relatively high frictional characteristics, to prevent sliding of the stock thereon. The conveyor mechanism itself is of a conventional nature, having upright side plates 41, 42, which define the "bed" of the conveyor. Rollers 44 extend between the side plates and support the belt 40, the return portion 40a of which is supported on top of secondary rollers 46, or the like. Belt 40 is driven, as stated above, by an independent drive 12a (seen in FIG. 1) of a conventional nature, including and electric motor, an electrically-actuatable magnetic or like clutch, and a gear head, which is coupled as by a chain drive to a belt-engaging-and-driving end roller 13.

As indicated above, the movable carriage 14 is freely movable along conveyor 12 and a preferred mounting for this is shown in FIG. 2. Basically, the upright side plates 41 and 42, which are themselves supported upon upright legs as illustrated in FIG. 1, each have inwardly-directed supports, 41a, 42a, respectively, upon which are fixedly secured an elongate rigid, cylindrical mounting and guide bar, 41b, 42b, respectively. The latter two elements support and guide the movable carriage 14, which is mounted thereon by mounting blocks or bosses 48 having cylindrical recesses therein, with "ball bushings" 50 disposed therebetween for providing effortless and essentially friction-free movement of the carriage along the conveyor bed.

The position of the carriage 14 relative to the conveyor 12 is readout by a rotary pulse generator 52 having output leads 53 which are ultimately connected back to computer 28, as by harness 14a. Pulse generator 52 is mounted by a suitable bracket upon the bottom portion of carriage 14 (FIG. 2) and has a sprocket 54 mounted on its input shaft. Sprocket 54 engages the links of a roller chain 56 which is fixedly mounted along an elongated right-angle bracket 58 secured to the lower extremity of side plate 42. Thus, as carriage 14 is moved along the conveyor bed, sprocket 54 is turned by engaging successive links in roller chain 56. As a result, the pulse generator 52 produces a continuing series of pulses which, by simple addition or subtraction, will always accurately determine the position of the carriage with respect to a predetermined point of origin.

The movable carriage 14 also includes a pair of oppositely-disposed flood lamps, or like light sources 60, 61, which shine through narrow mutually aligned slits 62 in each side of the carriage to cast a narrow plane of light which transversely intersects the bed of conveyor 12 and falls as a narrow line across the belt 40 thereof, or across a piece of lumber resting thereon, for example in the position illustrated in phantom at 64. Further, the carriage 14 includes a series (for example, four) of actuatable push buttons or like switches 66, 67 whose function will be explained hereinafter, and which are, like the rotary pulse generator 52, coupled back to computer 28 as by wiring harness 14a, through which operating power is also preferably provided for lamps 60, 61, etc.

It may also be observed that the conveyor 12, in the area of the examining station 10, has a series of spaced upright stock supports 68 extending upwardly from, and attached to, the top of conveyor side plate 42. These upright supports are provided for the purpose of supporting a piece of stock in the position of that shown at 65, (FIG. 2) used to examine the rear surface of the piece of stock which would otherwise rest atop conveyor belt 40 and thus escape examination. It is particularly for this function that two oppositely-disposed light sources are used, since in this manner the thin strip of light provided thereby will fall on each of the opposite sides of the stock as well as across the top surface thereof. The operator at the examining station will be on the side of the carriage having the controls 66, 67, and thus would normally be unable to see the opposite side of the piece of stock 65, illuminated by lamp 61. For this purpose, a mirror 70 is provided, mounted on the carriage across from the position of the operator.

Figure 3:
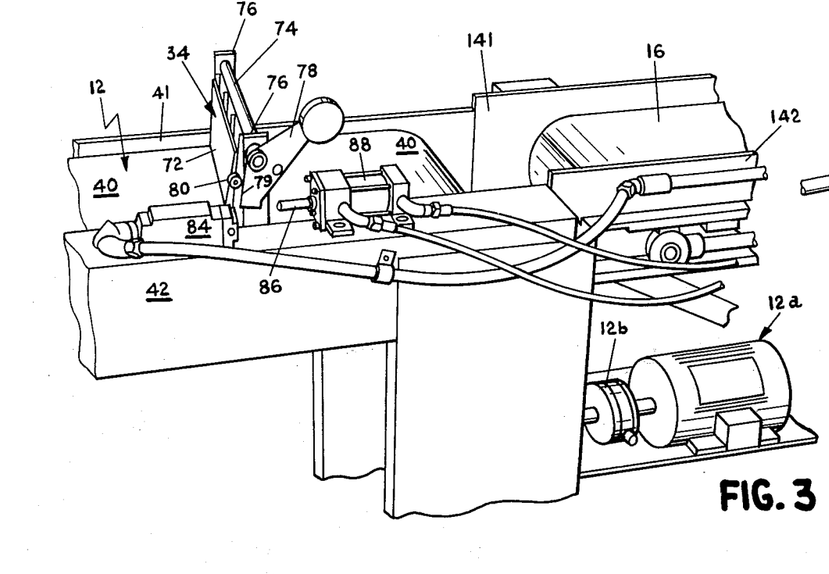
FIG. 3 is a fragmentary perspective view showing details of part of the lumber-handling apparatus.
Figure 3A:
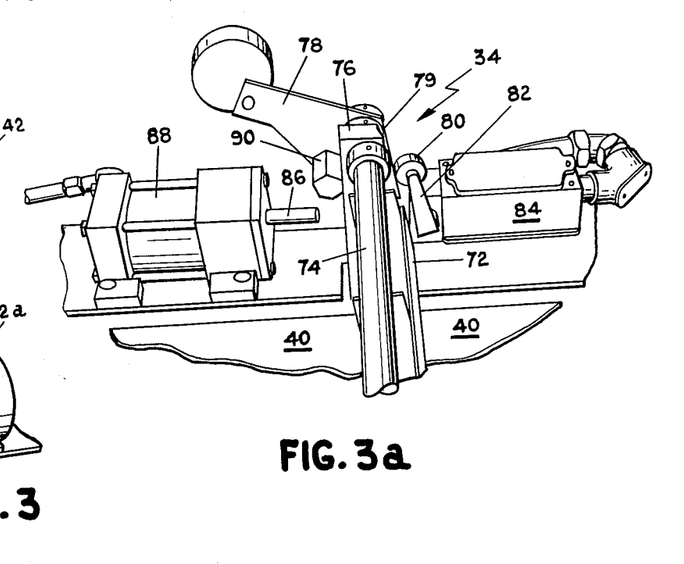
FIG. 3a is a further enlarged, fragmentary, perspective view showing part of the apparatus of FIG. 3.

The barrier means or gate 34 mentioned previously is seen in more detail in FIGS. 3 and 3a. As there shown, the gate includes a flat plate-like portion 72 which is suspended from a pivotal support rod 74 supported in upright mounting blocks 76 attached to the side plates 41 and 42 of conveyor 12. One end of pivot rod 74 projects through one of the mounting blocks 76, and a counterweight arm 78 is securely fixed thereto, in a manner normally holding the plate portion 72 rotated at least somewhat from a vertical position, i.e., swung upstream with respect to movement of the belt 40. An upstream-facing rear edge 79 of counterweight arm 78 provides a cam along whose surface moves a roller wheel 80 mounted on the upper end of a pivotal switch arm 82, the movement of which opens and closes the contacts (not shown) of an electrical switch unit 84. Ultimately, the switch 84 controls the drive 12a for conveyor 12, such that when the barrier plate 72 is moved to a vertical position, the drive 12a is interrupted, such as by actuating a magnetic or clutch 12b (FIG. 3) which responds to electrical control signals. In other positions of the barrier, switch 84 allows for operation of conveyor 12, i.e., motion of belt 40.

The downstream-facing side of the counterweight arm 78 comes into direct abutting contact with the end of the piston or plunger 86 of compressed air or like power cylinder 88 at such time as the barrier plate 72 is moved into a vertical position, to act as a physical stop which prohibits further movement of the plate under such conditions. Power cylinder 88 is of the type which normally holds a fixed position or "throw" of its piston until actuated, whereupon the piston is immediately drawn into the housing of the cylinder. Thus, it may be seen that with conveyor 12 operating and its belt 40 moving in the normal manner, a piece of lumber or other stock placed upon the belt will be moved downstream thereby until the downstream end of the piece of stock comes into contact with the barrier plate 72, whereupon the latter will be pushed by the stock into a truly vertical position. At this time, the counterweight arm 78 will come into contact with the plunger 86 of the power cylinder, and this will prevent any further movement of the barrier plate. At the same instant, however, the roller 80 and switch arm 82 will have moved a sufficient extent to actuate switch 84, thereby interrupting the drive for conveyor belt 40, as by actuating clutch 12b. Consequently, the piece of stock will be in a rest position, with its downstream end tightly against the barrier plate 72, and the latter in a true vertical position.

Subsequently, the cylinder 88 may be actuated by remote signal to sharply retract its plunger 86, and the same control signal for such operation may be used to actuate clutch 12b, to commence movement of conveyor belt 40. Under such conditions, the conveyor will immediately commence operation, the piece of stock will push the lower end of barrier plate 72 sufficiently downstream to allow movement of the piece of stock beneath the barrier plate (the conveyor force overcoming the counterweight) until the upstream end of that piece of stock has cleared the barrier, whereupon the counterweight will swing the barrier back to the upstream-inclined position shown in FIGS. 3 and 3a. In this position, a stop element 90 (FIG. 3a) attached to the inner side of counterweight arm 78 will come into abutment with mounting block 76, thereby limiting the extent of allowable upstream-swinging motion of the barrier plate at this position. At the same time, such movement of the counterweight arm will bring roller 80 and switch arm 82 into a position triggering switch 84, the output of which can be used to normalize the conveyor drive and, at the same time, to reactuate cylinder 88, such that the latter extends its piston 86 back to the position shown in these figures, blocking the barrier plate from being swung downstream past a vertical orientation.

As noted previously in connection with FIGS. 1 and 3, pieces of lumber leaving the examining station and conveyed onwardly by the operation of conveyor 12 pass onto the stock-advancing in-feed conveyor 16, which is also preferably a belt conveyor and which has its own separate drive means 16a. At the downstream end of conveyor 16 is the stock position-detecting gate 36 mentioned previously, as well as the stock-advancing-and-controlling roller drive means 22 noted previously, as well as the power saw installation 20.

Figure 4:
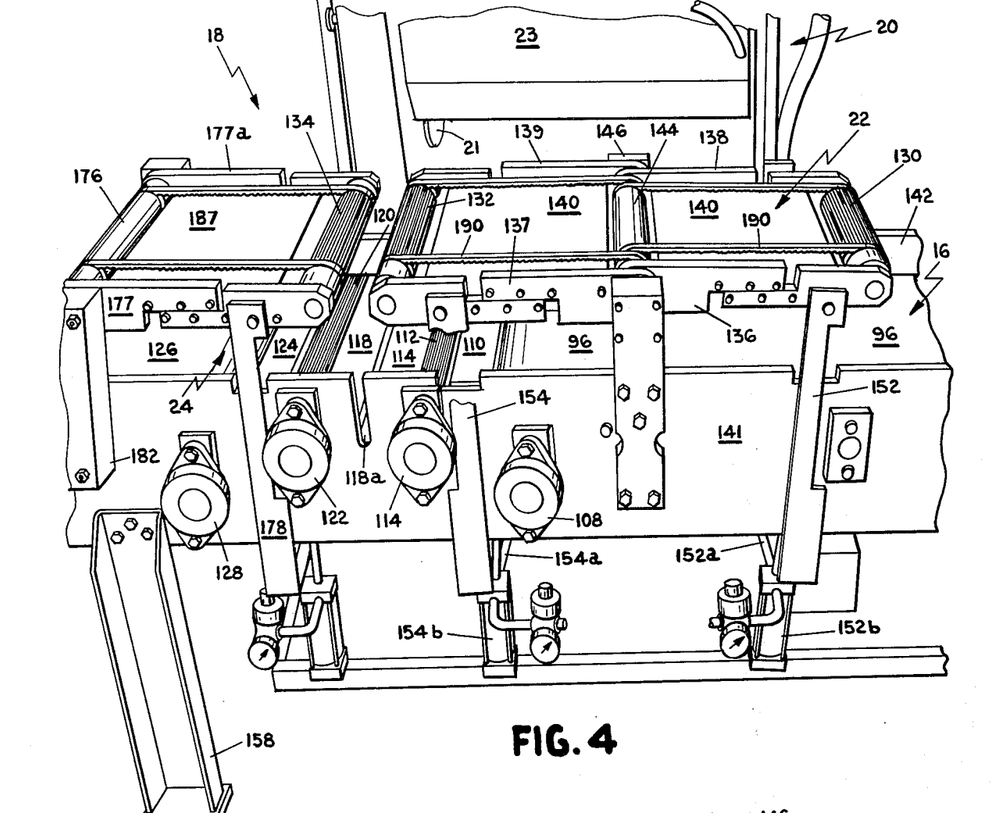
FIG. 4 is a fragmentary frontal perspective view showing portions of the stock-advancing apparatus at the cutting station.
Figure 4A:
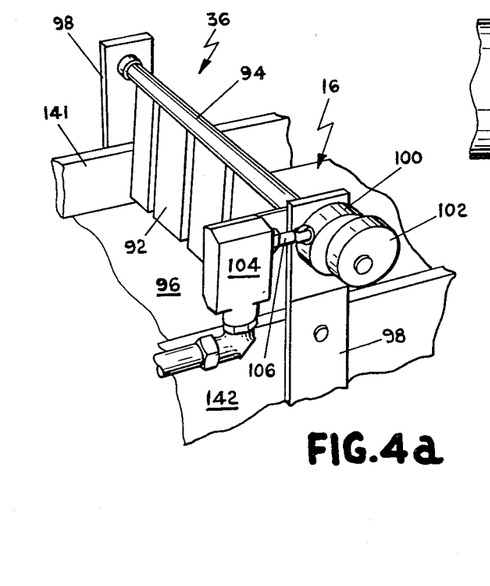
FIG. 4a is a fragmentary, perspective view, showing a stock presence-detecting gate used at the cutting station.

The stock position-detecting gate or barrier means 36 is shown in detail in FIG. 4a, and in a number of ways is structurally similar to the barrier means 34 discussed above. That is, this gate also includes a downwardly-depending plate portion 92 which is attached to a pivotally mounted rod or axle 94 so as to hang just above the surface of the belt 96 of conveyor member 16. The pivotal rod or axle 94 is journaled in upstanding support elements 98 which are themselves bolted to the upstanding sides 141, 142, which correspond to and which are in alignment with side plates 41 and 42 of conveyor 12, mentioned above. One end of pivot rod 94 projects through its bracket 98, and carries a switch-operating cam 100, as well as an eccentric counterweight 102, which is preferably set in a position to balance plate 92 away from a vertical position and angled at least somewhat in the upstream direction of conveyor 16. An electrical switch 104 mounted on side plate 142 has a projecting contact-actuating plunger 106 which carries a freely rotatable cam-follower wheel in its outer end, such wheel following the contour of cam 100 to make and break the contacts of switch 104. More particularly, switch actuation preferably occurs at the point when plate 92 is in a vertical position, being pushed there against the opposing force from counterweight 102 by each successive piece of stock traveling downstream on conveyor 16. In this manner, switch actuation will occur when the end of each succeeding piece of stock is at essentially the same point, i.e., in the vertical plane beneath pivot rod 94. This will be true regardless of the height (or thickness) of any given piece of stock, which otherwise would introduce errors by triggering the switch at different points for the same amount of travel past the vertical plane of rod 94, inasmuch as the thickness of the stock would then vary the radial distance from rod 94 at which the rotating force is applied to plate 92.

The actuation of switch 104, just described, provides a precise reference signal to the computer, signaling the instantaneous presence at a known reference point of the leading edge of each newly-arriving piece of stock as the same enters the area of the cutting station. As indicated above, the barrier means 36 is positioned directly upstream from the roller means 22, which with other apparatus now to be described carefully and precisely controls the incremental movement of the stock past the cutting station.

Figure 5:
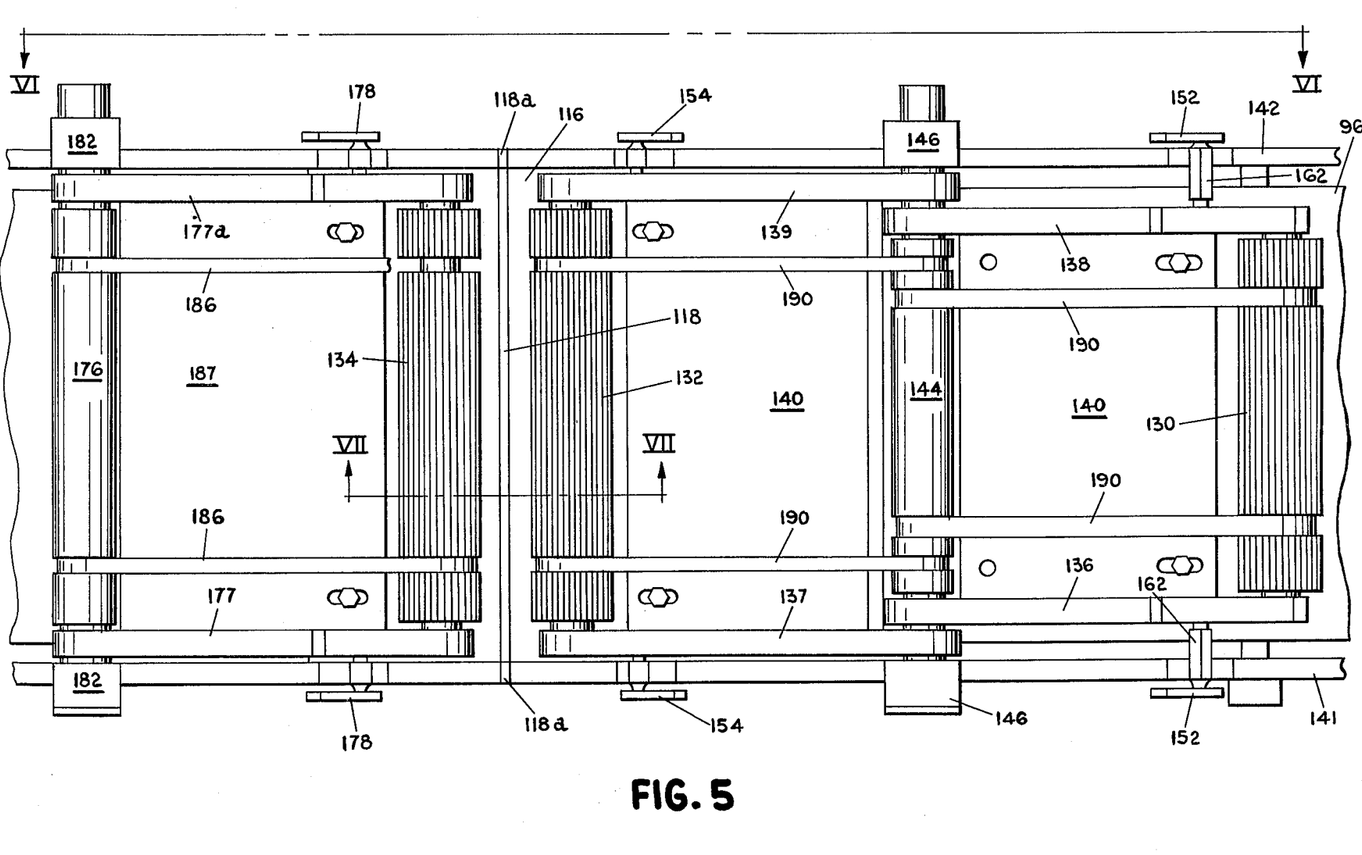
FIG. 5 is a fragmentary overhead plan view further illustrating parts of the apparatus as shown in FIG. 4.
Figure 6:
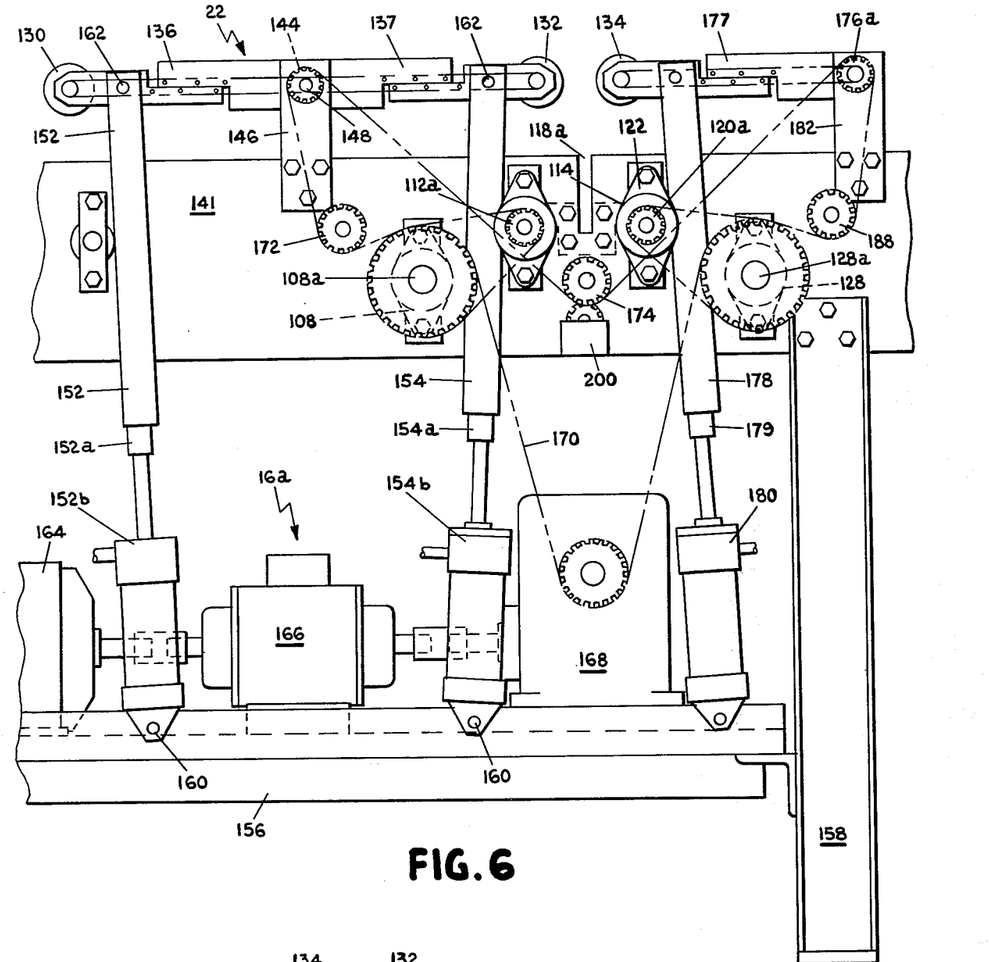
FIG. 6 is a fragmentary, side elevational view showing parts of the structure seen in FIGS. 4 and 5, taken along the plane VI-VI of the latter.
Figure 7:
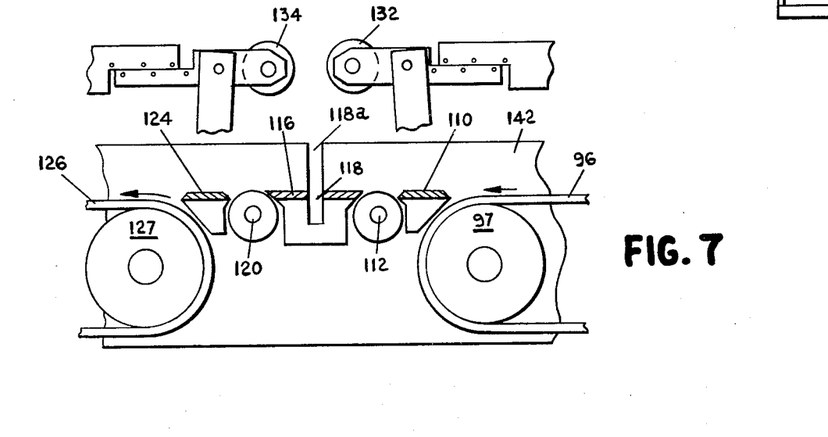
FIG. 7 is a fragmentary sectional elevation taken through the plane VII—VII of FIG. 5, showing details of certain of the stock-handling apparatus at the cutting station.

More particularly, the stock-advancing means at the cutting station is shown in detail in FIGS. 4, 5 and 6, to which reference is now made. At the cutting station, the conveyor 16 terminates in front of the saw installation 20, with belt 96 passing around a typical end roller 97 (FIGS. 1 and 7), journaled in bearing blocks 108 (FIG. 4) mounted in mutual alignment on both side plates 141 and 142, with belt 96 then returning back upstream, to the beginning of conveyor 16, immediately downstream from barrier means 34 (see FIGS. 1 and 3). At the downstream end of belt 96, stock passes over a support shelf or anvil 110 (FIGS. 4 and 7), is contacted and pushed onward by a roller 112 mounted in bearing blocks 114, crosses a cutting plate 116 having a central slot 118 which is in registry with corresponding slots 118a in side plates 141 and 142, and thence crosses and is pushed onwardly by another roller 120 which is journaled in bearing blocks 122. From this point, the stock passes over another support shelf or anvil 124 and onto the curving upstream extremity of a conveyor belt 126, which forms the operative member of outfeed conveyor 24, mentioned above. Conveyor 126 passes over an end roller 127 (FIG. 7) at this point, which is journaled in bearing blocks 128 (FIG. 4).

Movement of the stock in the above-described manner is not accomplished solely by the conveyor belts and rollers thus far named; on the contrary, another cooperating drive means is provided by the roller means 22, which is symetrically, oppositely disposed relative to, and spaced from, the conveyor belts and other stock-driving elements described above (i.e., disposed to act on the stock in a balanced oppositely-reacting manner with respect to conveyor 16 and rollers 112 and 120). That is, the roller means 22 includes three driven, position-shiftable, and stock-engaging rollers 130, 132 and 134 (FIGS. 4, 5 and 6), all of which serve to forceably drive the stock in concert with conveyor belt 96, roller 112, and roller 120, engaging the stock in a balanced pattern from the opposite side, and in coacting alignment with, the elements just named.

Figure 6A:
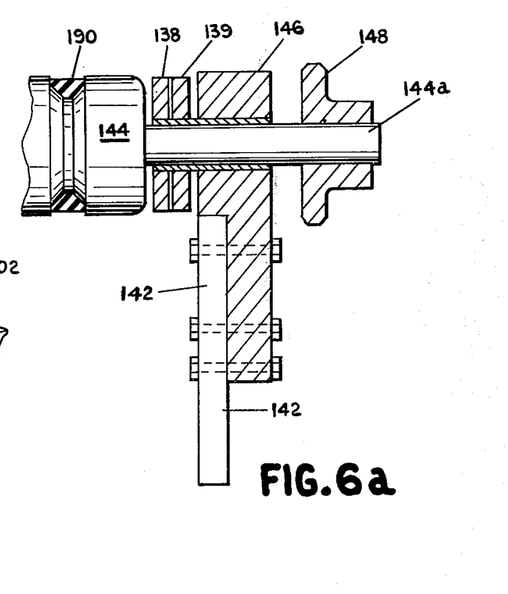
FIG. 6a is a fragmentary, enlarged elevational view, in central section, showing a part of the upper stockengaging and driving roller means.

Rollers 130 and 132 are part of the same basic assembly, being supported by and journaled between side plates 136 and 138, and 137, 139, respectively, such plates being themselves spaced apart by plate-like spacers 140 (FIGS. 4 and 5). Each such plate assembly is pivotally mounted at one end upon a shaft supporting a driving roller 144, such shaft being mounted for rotation in upstanding support blocks 146, which are in turn bolted to side plates 141, 142 of conveyor 116. This arrangement is illustrated in FIG. 6a wherein the side of the mechanism closest to the saw 20 is illustrated in detail. As there seen, the extended axial mounted shaft of drive roller 144 is designated 144a, and the same will be seen to carry a drive sprocket 148, which is to be keyed or otherwise non-rotatably mounted thereon so as to drive roller 144 whenever sprocket 148 is rotated. As illustrated, a common bushing 150 may advantageously be used for mounting roller shaft 144a in its upright support 146 and also in the side plates 138, 139. In this manner, shaft 144a will rotate within bushing 150 when driven by sprocket 148, while side plates 138 and 139 will pivot on the outside of this same bushing, for purposes related hereinafter.

Roller 134 is part of a separate structure like that of which rollers 130 and 132 are a part as just described. Thus, roller 134 is journaled in side plates 177, 177a (FIGS. 4 and 5) which are spaced apart by a plate 187. Side plates 177, 177a are pivotally supported upon a shaft which rotatably mounts a roller 176, by which roller 134 is drive, e.g., by belts or roller chain 186 connecting the two. Roller 134 may be shifted toward and away from the bed of conveyor 24 by arms 128 attached to side plates 177, 177a, and interconnected beneath conveyor 24 by an arm 179 (FIG. 6), the latter being connected to power cylinder 180 for movement thereby.

In accordance with the structure of the roller means just described, it will be observed that the upright mounts 146 and 182 fixedly establish the position of drive rollers 144 and 176 with respect to conveyor belts 96 and 126. The same is not true with respect to the driven, position-shifting rollers 130, and 132 and 134, inasmuch as their respective side plates are pivotal about the axis of rollers 144 and 176, such pivotal movement being controlled by upright arms 152 (for roller 130), and 154 (for roller 132) and 178 (for roller 134). Such upright arms are attached to side plates 136, 138 in oppositely-aligned pairs, and interconnected beneath the bed of conveyor 16 by cross members 152a, 154a and 179 respectively, so as to form generally U-shaped structures.

Each of the U-shaped structures just described is controlled by a separate pneumatic power cylinder (FIGS. 4 and 6) 152b, 154b, or 180 respectively, such that downward movement of the corresponding power cylinder piston or plunger will pivot roller 130, 132 or 134 downwardly, to pinch the stock tightly against the structure aligned therebeneath. In the case of roller 130, the structure aligned beneath is conveyor belt 96; in the case of roller 132, the aligned structure is roller 112, and in the case of roller 134 the aligned structure is roller 120. As illustrated (FIG. 6) power cylinders 152b, and 154b and 180 may be mounted upon a lower support table structure 156 mounted on legs 158 which serve to support the conveyors by their side plates. Preferably, the power cylinders are pivotally mounted by pins 160, so that they may rock at least alightly to accommodate the consequent movement of arms 152, 154, or 178 which are themselves pivotally attached to the side plates of the roller means, as by pins 162.

The drive means 16a for conveyor 16 may also be mounted on the lower support table 156 (FIG. 6), and may include a motor 164 whose output shaft is coupled to a magnetic or other electrically-actuatable clutch device 166 which, in turn, is coupled to a gear head 168, all such components being of a conventional and known nature. The output from gear head 168 is preferably coupled as a common drive to infeed conveyor 16, outfeed conveyor 24, intermediate rollers 112 and 120, and also to the upper roller means 22. This may advantageously be accomplished by use of a single continuous drive chain 170 (FIG. 6) which extends from gear head 168 around a suitable drive gear 108a mounted on the shaft journaled in bearing block 108 actuating the drive roller for conveyor 16, thence around a gear 112a on the extended end of roller 112 journaled in a bearing block 114, thence around an idler 172, then upwardly around drive sprocket 148 for roller 144, downwardly around an idler 174, then upwardly around a drive sprocket 176a for driven roller 176, then around an idler 188 and then around an appropriate drive gear 120a on the extended end of driven roller 120, journaled in bearing block 122, after which the chain is entrained about a gear 128a on the end of the driven shaft journaled in bearing block 128 (driving conveyor belt 126 from its upstream end), following which the chain is returned to gear head 168.

In accordance with the arrangement just described, it will be clear that every increment of movement of the drive chain 170, in response to corresponding drive movement of the output from gear head 168, will be transmitted equally and substantially simultaneously to all of the different components which comprise the stock-advancing means at the cutting station. Furthermore, because rollers 130 and 132 are coupled in drive relation with driven roller 144, as by the illustrated belts 190 or by other means such as drive chains (not illustrated), and roller 134 is coupled in like manner to driven roller 176, there will be complete uniformity of drive motion, with driven rotation of roller 130, for example, equaling the driving movement of conveyor belt 96, and with a like relationship between roller 132 and roller 112, as well as between roller 134 and roller 120, with all such driven movement coming from the same source, i.e., drive chain 170 and gear head 168.

This driven movement may thus be monitored at any point in the drive train, as for example at any point along chain 170. For example, the gear or roller 174, described above as an idler, may also serve as an actuator or drive gear directly analogous to that designated 54 in FIG. 2 and described in connection with rotary pulse generator 52 of that figure. In this manner, a direct and very reliable input may be obtained representative of the movement of stock past the cutting station and, in particular, past the slot 118, 118a, through which a powered saw blade 21 (FIG. 4) moves upon forward and rearward reciprocation of a movable head 23. Such a saw unit is a known type, preferably the type available from Oliver Machinery Co., Grand Rapids, Michigan, designated model 94.

The accuracy of an output taken from drive chain 170, as just described, will be completely reliable so long as there is no slippage between the stock and the driving elements, and the drive structure which has been described is particularly advantageous in this regard. That is, conveyor belt 96 is, as stated above, preferably of the type having a rubbery or rubber-like, resilient surface which has excellent frictional characteristics. The driven rollers 130 and 132 (as well as rollers 134, 112, and 120) are all preferably of steel or the like, and thus are essentially rigid. Thus, there can be no diametrical compression of these rollers, as would change their effective drive circumference, even when the rollers are forced tightly against the lumber. Further, as indicated by the drawings, each of these rollers is longitudinally ridged with fine serrations or flutings, preferably of gear-like cross section. This surface configuration gives excellent frictional engagement with the stock, particularly when the stock is similarly engaged on its opposite side, or when the stock is resting on the somewhat resilient conveyor belt 96. Thus, there will be no slippage when the different drive elements engage the stock and move it along. Furthermore, because of the absence of any diametrical distortion of the drive rollers the effective drive diameter thereof always remains the same, so that each increment of their rotation will be faithfully reflected in a corresponding increment of longitudinal movement of the stock.

In operation, the lengths of the different pieces in a desired manifest or list of lumber or the like are entered into the computer, by operation of the teletype or other such data input terminal 30, with the computer preferably being programmed to provide a printout of the manifest actually entered in the computer at any desired time, upon an appropriate command entered by actuation of the teletype. When the desired manifest has been completely entered, the appropriate bias should be selected, by entry of a command from the teletype unit. Also, the computer can readily be used to control the saw so as to automatically cut scrap into shorter lengths, if desired, and if such a program feature is included, a control should be provided so that the operator may select the maximum stock length which the computer is to allow without commanding a cut to be made. The bias factor just mentioned represents the allowable amount of wasted good lumber which will be willingly sacrificed upon every cutting sequence between defects, with the computer being programmed to compute for the optimum yield of pieces, based upon the allowable bias which has been selected, and considering each successive piece of raw lumber which is examined, at examining station 10, relative to the manifest which has been entered.

In computing the optimum yield, priority can be given to length only, quantity only, or a combination of both. If priority has been given to length only, as may typically be the case, the optimum yield will be that combination of cut pieces which produces the longest lengths with the minimum waste, within the bias which has been set. The selecting of a bias is an important part of the computer program, since it affects the logic function of the computer and will change the yield obtained from a given quantity of stock. Basically, upon receiving the defect or length in formation from the examining station, the computer will compute complete tables of possible cutting variations which could be made on the piece of stock, tabled according to length, with the longest lengths first. The table is then scanned and compared to the bias selected, and the first variation produces scrap which within the bias will be the one selected. That variation, thus, will produce the combination of pieces containing the longest possible lengths, within the selected bias. For purposes of illustration, if it be assumed that the manifest was composed of lumber with lengths of 30 inches, 24 inches, 20 inches, and 14 inches, and the particular piece of lumber under examination had a span of 54 inches between defects (herein defined as split, imperfectly cut, or otherwise imperfect end extremities, as well as any of the typical defects such as knots and the like between end extremities), the computer would be programmed to always select only the two longest pieces, i.e., one 30 inch and one 24 inch, at least until the total quantities of such lengths requested in the manifest had been filled, following which the combination of the next longest pieces would be chosen.

This example completely neglects the loss of lumber incurred at each saw kerf, however, and is of course highly simplified; thus, it is of only limited value for purposes of illustration. Considering the loss of saw kerf (which may be made a selectable input to the computer, to provide for use of different saws, etc.), with the facts of the foregoing example, if it be assumed that the saw kerf is ⅛ inch, the optimum yield would no longer be one piece 30 inches long and another piece 24 inches long, since this combination exceeds the available length when the kerf loss is considered. Instead, the optimum yield becomes one 24 inch piece and two 14 inch pieces, since this wastes only 1⅝ inches of stock. If, however, the bias for the computer had been set at four inches of allowable waste, the optimum yield would no longer be that just stated, but would instead be one 30 inch piece and one 20 inch piece, with a waste of 3¾ inches of stock, inasmuch as this combination produces longer pieces.

As stated above, priority can be given to factors other than length in programming the computation of optimum yield as for example, quantity of pieces. That is, if the manifest comprises a great number of pieces of the same dimension, together with far fewer pieces of different dimensions, the predominating length or lengths can be given priority so that the computer will choose that length (or lengths) in dis-regard of other factors such as longest length when the occasion arises, as when the other considerations are equal. Also, such priorities can be weighted, so as to take precedence in a given order, or in a given percentage of the cycles of operation or computation. For example, the length priority can be weighted to occur until a certain percentage of the manifest has been completed, or a certain percentage of the longer lengths obtained, following which the quantity priority may be given effect, whether for all of the remaining manifest or only a portion thereof. Thus, in accordance herewith the phrase "optimum yield" should be understood as meaning that yield which by computation produces the least waste within the programmed priorities.

The examination of lumber at examining station 10 thus proceeds on a piece-by-piece basis, with a supply of lumber being brought to the examining station in any desired manner, as for example, by conveyor. The examiner takes each piece individually and places it on conveyor 12, whereupon the piece is conveyed downstream until one end comes into abutment with barrier 34, pushing the plate 72 thereof (FIG. 3) into a vertical position, whereupon the barrier stops the progress of the stock by operation of power cylinder 88 and switches off the conveyor 12 by operation of switch 84, as explained above. Operation of barrier 34 in the manner just stated, with consequent stopping of the conveyor 12, signals the computer that a piece of stock is in position for examination, and the position of the gate or barrier establishes a zero reference point for length measurements. The operator then moves the carriage 14 along conveyor 12, typically (but not necessarily) starting at the forward end of the stock, sending a series of successive keying signals to the computer to identify the position of the zero point or origin, as well as the location of each defect. This is accomplished by moving the carriage 14 until the thin line of light emanated through the slits 62 lies directly at the point to be signalled, as for example the leading or trailing edge of the defect, and at such point, triggering one of the controls 66, 67 (FIG. 2). In this regard, it may be pointed out that one such control may be dedicated for use only in signalling the zero point, and another only for signalling other points. Also, it is useful to have a light or other such indicator on the carriage by which the operator may be shown that each keying signal has been received by and entered into the memory of the computer, and the controls should also include one by which entered keying signals may be erased or deleted when desired.

It is expected that each end of each piece of stock will have some defect, and there will thus always be a defect marking near each end. Intermediate the ends, there can be any number of defects, each of which is "marked" in the foregoing manner. In this respect, it should be noted that the operator need not of necessity start at any particular point along the piece of stock, since with the computer signaled that a piece of stock is in position against barrier 34, and the zero reference point established, the rotary pulse generator 52 will send signals to the computer regardless of the particular direction of motion of the carriage 14, and such signals may easily be coded (as by polarity) in accordance with the direction of carriage travel so that the signals may readily be added and subtracted on an instantaneous basis. Therefore, the computer will alwyas "know" the position of the carriage 14 with complete accuracy, and every triggering of the appropriate control 66, 67 will merely cause a given length-representative pulse signal to be entered into the computer memory.

It should be pointed out that the operator merely examines each piece of stock for defects, and signals only this information to the computer, making no decision (or even having to think about) the position of desired cuts between defects. All of the latter is computed by the computer, in arriving at the optimum yield decisions mentioned above. All the operator need do is move the carriage 14 once over the entire length of each successive piece of stock, signaling the conveyor for the upstream and downstream boundaries of each defect. When each piece has been completely examined in this manner, the operator actuates a particular one of the controls on the carriage, whose function is to signal the computer that examination is complete for that piece of lumber and cause actuation of the gate means 34, whereupon power cylinder 88 retracts its plunger and conveyor 12 is switched on, moving the examined piece of stock downstream, tilting gate 34 out of the way. In this manner, the examined stock is moved onto conveyor 16.

Each successive piece of stock from the examining station will thus be conveyed downstream by conveyor 16, past the sensor gate 36 and on to the cutting station 18. During a brief instant of the interval required for this travel, the computer computes the optimum yield for cutting that particular piece of stock, based on the examining information just entered into the computer, so that incremental stock-advancing movement at the cutting station, together with the actual cutting, may ensue directly. As the stock contacts the gate 36, it will be remembered that switch 104 signals this event to the computer at the instant the barrier plate 92 (FIG. 4a) is in a true vertical position. Based on the known speed of conveyor belt 96, and the known position of the stock-sensing barrier 36, the moment can readily be determined when the stock passes under roller 130 and, whether by a timed delay device or by signal from the computer, power cylinder 152b (FIGS. 4 and 6) is thus actuated at the proper time to pivot arms 136 and 138 downwardly and bring roller 130 tightly into contact against the top of the stock, clamping the same against conveyor belt 96 but, at the same time, cooperatively driving the stock onwardly with the conveyor belt, at the same speed as the latter. Following this, and making use of the position information obtained by monitoring movement of drive chain 170 after the signal from switch 104, the computer calculates when the downstream end extremity of the piece of stock passes beneath roller 132, and at the proper instant the computer triggers power cylinder 154b into operation, whereupon arms 154 are moved downwardly, pivoting side plates 137 and 139 downwardly and bringing roller 132 downward into contact with the upper surface of this stock, in effect pinching the stock between roller 132 and roller 112, directly upstream of the slot 118, 118a, which the saw blade 21 moves in cutting the stock.

With the stock thus rigidly retained in position while at the same time being driven downstream in a controlled manner, the computer will cause the driven movement of the stock to stop at the proper place for cutting to eliminate the first defect, normally at the forward end extremity. As described above, this is accomplished by coupling the appropriate signal from the computer to the clutch 166, whereupon all drive of the stock ceases (although the characteristic inertia of the drive train should be taken into consideration). A very desirable refinement in this basic control routine is to implement the drive motor 164 by using a variable-speed, or at least two-speed, motor which has a normal drive speed and a slower speed, with a control which responds to particular control signals by selecting which such speed will be in effect. Using such an arrangement, the computer can readily be programmed to call for the slower speed a given distance before the stock has advanced to the actual position where a cut is to be made, i.e., where the stock is to be stopped. Thus, for example, as the lumber moves past the cutting slot, approximately six inches prior to the arrival of the actual location for a cut, the computer can call for a reduction of one-half in the normal speed (which may be on the order of one hundred feed per minute), to enhance accuracy in the immediately subsequent stopping of the drive by which the stock is to be accurately placed in position for cutting. In such an arrangement, if the next ensuing cut was scheduled for less than six inches away, the drive would merely continue at the slow speed after the first cut, until the stock was stopped again, for the second cut. Variations in this approach are also possible, as for example using a variablespeed motor and a gradual or continuing slowdown at a given rate prior to each cut. In any event, when the signal is given by the computer to stop movement of the stock, the computer also signals the operation of the saw 20, which then makes the first cut, with the stock accurately positioned over the cutting slot 118, and fixedly held in the desired position by the rollers 130 and 132, through operation of power cylinders 152*b* and 154*b*.

In making the first cut, the third roller in the series thereof, that is, roller 134, may or may not be actuated downwardly by its controlling power cylinder 180, since the distance at which the first cut should be made relative to the end of the stock will vary from piece to piece, and may or may not be sufficient to position the end of the piece downstream from roller 134. The computer should be programmed to command the downward shifting of roller 134, through actuation of its power cylinder 180, as a function of the location of the first cut for a given piece of stock, such that roller 134 will stay up, in the position shown in FIG. 6, unless the downstream end of a given piece of stock is at least a predetermined minimum distance downstream from this roller when the stock has been properly stopped and positioned over slot 118 for the first cut.

The computer then continues commanding the incremental, step-by-step movement of the stock past the cutting slot 118, stopping the drive each time a point on the stock becomes positioned over the cutting slot (allowing for inertia) cutting in accordance with the previously-computed and stored schedule of the cuts for that particular piece which will produce the optimum yield. Once again, the relative position of the piece of stock is continuously monitored by reading out movement of the common drive chain 170, as by the use of a rotary pulse generator which may, for example, be driven by the shaft of idler 174, directly beneath the cutting slot 118, as indicated for purposes of illustration by the numeral 200 (FIG. 6). Since the length of each piece of stock is also signaled to the computer at the examining station, the computer can readily control the different parts of the stock-advancing roller means as necessary in accordance with the approach and passing of the upstream end of each board. That is, when the upstream end of each piece closely approaches roller 130, the computer actuates power cylinder 152*b* to raise this roller. The same is true with respect to rollers 132 and 134, although these must be controlled in relation to the position of the final cut to be made, which requires the rollers to hold the stock firmly in position for cutting. Thus, rollers 132 and 134 are desirably positioned as close as possible to the cutting slot or channel 118, for the best possible control of stock in the making of cuts near the upstream end extremity thereof, where it may at times occur that roller 132 will have been lifted from the stock and the end extremity thereof moved beyond this point when the final cut is made. Under these circumstances, roller 134 will still forceably engage the stock and hold the same in position for the final cut, following which roller 134, and its driven counterpart roller 120, will operate to drive the stock away from the cutting station until the last possible moment, when the end of the stock begins to pass under roller 134, at which time the computer will command power cylinder 180 to raise roller 134. Any remaining small pieces of stock present at this point can readily be pushed onward by the downstream end extremities of the next succeeding piece of stock to pass through the cutting station.

It should be pointed out that, although not particularly illustrated in the drawings or otherwise described herein, it is distinctly a part of the invention to utilize the computer, including the input terminal, to control more than one cutting station and saw unit, each typically having its own examining station, complete with conveyor, etc. This is because the speed of the computer is so much greater than the examining and cutting operations that the computer may very readily be time-shared in a multiple installation having numerous examining and cutting stations, so long as the computer embodies sufficient memory capacity and is programmed to maintain the required individuality between systems.

It is entirely possible that after examining the foregoing disclosure, those making use of the invention may employ embodiments of the concepts involved which differ somewhat from the particular embodiments shown and described herein, or may make various changes in structural details to the illustrated and described embodiments. Consequently, all such changed embodiments or variations in structure which utilize the concepts of the invention and embody the spirit thereof are to be considered as within the scope of the claims appended herebelow, unless these claims by their language specifically state otherwise.

The embodiments of the invention in which an exclusive property or privilege is claimed are defined as follows:

1. A computer-controlled stock-cutting system comprising in combination: an electronic computer means for producing optimum-yield cutting commands based on stock defect location information and at least one dimension of different required pieces; a stock examining station, including means for supplying stock defect location information to said computer upon examination of stock; a cutting station, including means for cutting the stock; and drive means controlled by said computer means and having portions for contacting said stock and controlling its movement and position, by moving while contacting the stock to transport stock past said means for cutting, by stopping to thereby stop the stock relative to the cutting means at positions determined by said computer means where cutting is to take place, and for holding the stock securely where so stopped by sustained stationary contact therewith, whereby the stock may be automatically moved and positioned, and cut, at places on the stock whose position is established by said cutting commands from said computer.

2. The stock-cutting system defined in claim 1, wherein said means for cutting the stock is controlled by said computer means and is automatically actuated by certain of said cutting commands determined thereby to cut said stock upon said stopping and holding of the latter.

3. The apparatus as defined in claim 1, wherein said means for transporting stock includes a conveyor having a switchable drive controlled by said computer means.

4. The apparatus as defined in claim 3, wherein said conveyor drive includes at least a motor and a clutch, and said clutch is controlled by said computer means.

5. The apparatus as defined in claim 3, wherein said means for transporting stock also includes at least one roller means disposed above said conveyor for contacting stock on a side thereof other than that in contact with the conveyor; and including means for driving said roller means at substantially the same stock-moving rate as that of said conveyor.

6. The apparatus as defined in claim 5, including means controlled by said computer for stopping and starting stock-driving operation of said roller means.

7. The apparatus as defined in claim 5, including means controlled by said computer for shifting said roller means into and out of stock-engaging position.

8. The apparatus as defined in claim 5, wherein said means for driving said roller means and said conveyor drive have at least one common, shared drive train component.

9. The apparatus as defined in claim 8, wherein said common component includes a clutch controlled by said computer means.

10. The apparatus as defined in claim 3, wherein said conveyor includes a movable member whose extent of movement has a known relationship to the extent of movement of stock on said conveyor means, and a pickoff means for monitoring movement of said movable member and providing signals to said computer means which have a known relation to the extent of movement of said member.

11. The apparatus as defined in claim 10, wherein said conveyor has an endless belt-type conveying element and includes means coupling said movable member to said conveying element for movement therewith.

12. The apparatus as defined in claim 11, wherein said movable member comprises a drive chain coupled in driving engagement with said conveying element.

13. A method of automatically cutting stock to remove defects and to divide the remaining stock into an optimum combination of different pieces, comprising the steps: examining the stock and producing data input signals representative of the amount of acceptable stock located between particular selected defects thereon; using an electronic computer to determine where said stock should be cut to to product the optimum yield of defect-free pieces of said stock corresponding in at least one dimension to at least some of those on a previously-established manifest, with minimum waste relative to a previously-established waste allowance standard and as a function of said data input signals and the known dimension requirements in said manifest and of said waste standard; using output signals from the computer representative of the stock-cutting determinations made thereby to effect control of stock-engaging remotely controllable drive means and thereby move the stock relative to a stock-cutting apparatus and automatically bring the stock into such positions of relative alignment with the cutting apparatus as are required for cutting of the stock in accordance with said computer determinations; using such computer output signals to control remotely-actuable mechanical means for holding the stock securely and non-movably in said positions of relative alignment during cutting of the stock; and controlling said cutting apparatus by use of said computer to cut said stock at said positions of relative alignment determined by said computer.

14. The method defined in claim 13, wherein said computer is used to effect control of said stock movement by stopping and starting the operating movement of a conveying apparatus by which said stock is transported.

15. The method as defined in claim 14, wherein said computer is also used to reduce the speed of operating movement of said conveying apparatus from a normal speed to a lower speed during a predetermined interval prior to stopping for cutting of said stock at said positions of alignment.

16. The method as defined in claim 13, wherein said computer is operated by using a manually actuable input device, and including the step of varying the said stock-cutting determinations of said computer by operating said input device to change said previously-established waste allowance standard, of which such determinations are a function.

17. The method as defined in claim 13, including the step of using said computer to control a peripheral print-out means and thereby produce a then-current listing of pieces which have at such time been cut in satisfaction of said manifest list.

18. The method as defined in claim 13, wherein said step of using said computer includes using an input keyboard means to enter data into said computer relating to said manifest list.

19. The method as defined in claim 18, including the step of using said computer to control a peripheral print-out means after entering said data, to thereby produce a print-out list of the pieces in the said manifest, for verification and the like.

20. The method as defined in claim 18, including the step of using said computer to control said print-out means after entry of said manifest data and after examination and cutting of at least some stock, to produce a then-current print-out list of pieces which have then been cut in satisfaction of said manifest list.

21. The method as defined in claim 18, wherein said steps of using an input keyboard means and of using said computer to control a print-out means comprise using a remotely controllable typewriter-like device both as an input device and as a printout device.

22. A method of automatically cutting stock to remove defects and to divide the remaining stock into an optimum combination of different pieces, comprising the steps: examining the stock and manipulating control means to cause data signals representative of the position of defects on the stock to be inputed to an electronic computer; using a manually-controllable input device to operate said computer by conditioning it to use a particular one of several selectable waste allowance standards in computing optimum-yield stock-cutting determination; using said computer to determine where said stock should be cut to produce the optimum yield of defect-free pieces corresponding in at least one dimension to at least some of those on a previously-established stock manifest on the basis of minimum waste relative to said particular wasted allowance standard and as a function of said inputted data signals and the known dimension requirements in said stock manifest; using output signals from the computer representative of the stock-cutting determinations made thereby to effect control of stock movement relative to a stock-cutting apparatus and thereby bring the stock into such positions of relative alignment with the cutting apparatus as are required for cutting of the stock in accordance with said computer determinations; and controlling said cutting apparatus by use of said computer to cut said stock at said positions of relative alignment determined by said computer.

* * * * *

UNITED STATES PATENT AND TRADEMARK OFFICE
CERTIFICATE OF CORRECTION

PATENT NO. : 3,941,019
DATED : March 2, 1976
INVENTOR(S) : Ralph B. Baldwin
James T. Visser It is certified that error appears in the above-identified patent and that said Letters Patent are hereby corrected as shown below:

Column 1, Line 61;
"defecting" should be ---"defecting"--- (in quotes)

Column 2, Lines 51 and 52;
"Stockengaging" should be ---stock-engaging---.

Column 3, Line 3;
"cabinetenclosed" should be ---cabinet-enclosed---.

Column 4, Line 6;
"readout" should be ---read out---.

Column 7, Line 8;
After "conveyor" insert ---belt---.

Column 7, Line 40;
"mounted" should be ---mounting---.

Column 9, Line 60;
"bias" should be ---"bias"--- (in quotes)

Column 9, Line 68;
"bias" should be ---"bias"--- (in quotes)

Column 11, Line 2;
After "when" omit ---the---.

Column 12, Line 9;
"optimum yield" should be ---"optimum yield"--- (in quotes)

UNITED STATES PATENT AND TRADEMARK OFFICE
CERTIFICATE OF CORRECTION

PATENT NO. : 3,941,019
DATED : March 2, 1976
INVENTOR(S) : Ralph B. Baldwin
James T. Visser It is certified that error appears in the above—identified patent and that said Letters Patent are hereby corrected as shown below:

Column 13, Line 26;
"variablespeed" should be ---variable-speed---.

Column 13, Line 55;
after "inertia)" insert---for---.

Column 15, Line 64;
Amendment B, Claim 54, Line 8
"to to product" should be ---to -- product --.

Signed and Sealed this

Third Day of August 1976

[SEAL]

Attest:

RUTH C. MASON
Attesting Officer

C. MARSHALL DANN
Commissioner of Patents and Trademarks